United States Patent [19]

Cresswell et al.

[11] 4,146,713
[45] * Mar. 27, 1979

[54] METHOD OF PREPARING 3-MORPHOLINO-2-CYANOACRYLAMIDE

[75] Inventors: Ronald M. Cresswell, Raleigh; John W. Mentha, Washington; Russell Seaman, Chapel Hill, all of N.C.

[73] Assignee: Burroughs Wellcome Co., Research Triangle Park, N.C.

[*] Notice: The portion of the term of this patent subsequent to Jun. 27, 1994, has been disclaimed.

[21] Appl. No.: 507,814

[22] Filed: Sep. 20, 1974

Related U.S. Application Data

[60] Continuation-in-part of Ser. No. 244,305, Apr. 14, 1972, Pat. No. 3,864,341, which is a division of Ser. No. 781,590, Dec. 5, 1968, Pat. No. 3,682,957.

[30] Foreign Application Priority Data

Feb. 2, 1968 [GB] United Kingdom ............... 5397/68

[51] Int. Cl.$^2$ .................... C07D 49/02; C07D 295/00
[52] U.S. Cl. .................................................. 544/163
[58] Field of Search ......................................... 544/163

[56] References Cited

U.S. PATENT DOCUMENTS

| | | |
|---|---|---|
| 3,141,018 | 7/1964 | Straley .................................. 544/163 |
| 3,310,555 | 3/1967 | Pesson .................................. 544/163 |
| 4,051,242 | 9/1977 | Klemm et al. ....................... 544/163 |

*Primary Examiner*—Paul J. Killos
*Attorney, Agent, or Firm*—Donald Brown

[57] ABSTRACT

A compound

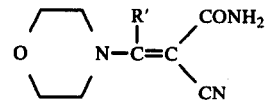

where R' is hydrogen or lower alkyl, the compound being usable as an intermediate in the preparation of 4-hydroxypyrazolo [3,4-d]pyrimidine (Allopurinol) and its useful relatives.

A method of preparing

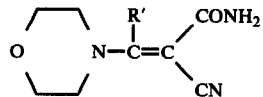

which comprises reacting R'C(OR)$_3$, morpholine and cyanoacetamide where R' is hydrogen or lower alkyl and R' is lower alkyl.

7 Claims, No Drawings

METHOD OF PREPARING 3-MORPHOLINO-2-CYANOACRYLAMIDE

This application is a continuation-in-part of U.S. application Ser. No. 244,305 filed Apr. 14, 1972, now U.S. Pat. No. 3,864,341 which is a division of U.S. application Ser. No. 781,590, filed Dec. 5, 1968, now U.S. Pat. No. 3,682,957. This application only discloses and claims subject matter to be found in the aforementioned U.S. application Ser. No. 244,305 and U.S. application Ser. No. 781,590.

This invention is directed to new morpholino cyanoacrylamide compounds and methods for their preparation, and to methods of preparing useful pyrazolo[3,4-d]pyrimidine derivatives therefrom.

One of the useful compounds which is prepared according to the methods of this invention is 4-hydroxypyrazolo[3,4-d]pyrimidine (I),

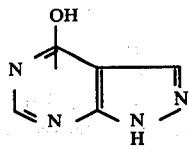

also known as Allopurinol, which is useful as an inhibitor of the enzyme Xanthine oxidase, in vivo and which is also useful in the treatment of gout.

Allopurinol is a drug which is normally administered to humans in relatively large doses (i.e. 100-800 mg) per person per day and is generally given over extended periods.

Thus the purity of the product is of extreme importance, more so than with most pharmaceuticals, since undesirable contaminants may have a cummulative detrimental effect if taken over extended periods of time.

Therefor there has developed the need for not only an economical method of preparing Allopurinol, but also a method whereby Allopurinol could be prepared in a satisfactory pure state without the need of using excessive and expensive purification steps.

The methods and compounds of this invention are also useful in the preparation of other useful pyrazolo pyrimidine derivatives reported in the literature, such as 4,6-dihydroxy pyrazolo(3,4-d)pyrimidine.

A number of methods of synthesis are known for producing Allopurinol (I), for example:

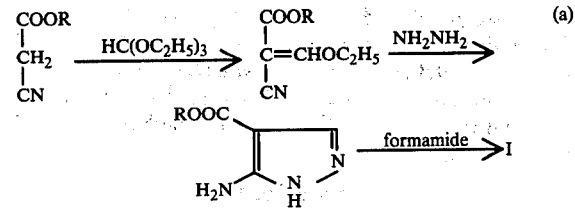

Where R is an alkyl, for example ethyl;

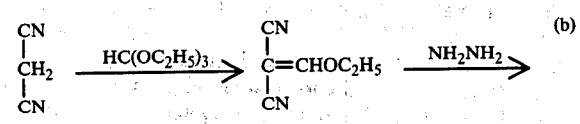

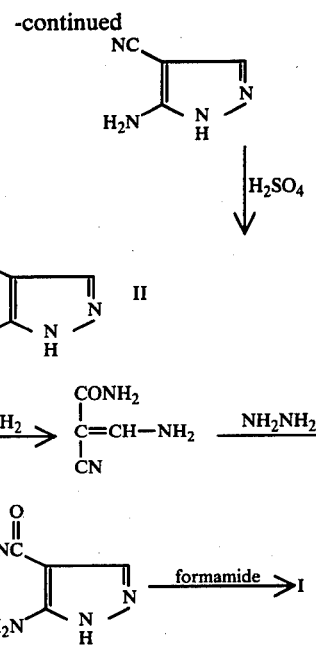

This is the route from cyanoacetamide and formamidine disclosed in U.S. patent application Ser. No. 651,393 filed July 6, 1967 and assigned to assignee of this application.

Method (a) noted above, although providing Allopurinol in good yield, produces a product with considerable colored contaminants which are expensive to remove. These colored contaminants arise, at least in part, because the final ring closure in formamide requires temperatures in excess of 160° C. where decomposition is known to occur. This is also an inconvenient temperature for large scale manufacture as it is not readily achieved using super-heated steam.

Method (b) noted above is long, costly and the intermediate (II) used in the final step requires recrystallisation before it can be used to make satisfactory Allopurinol even though the temperature in the final step is only 140°-145° C. In addition the products from the reaction of ethylcyanoacetate and triethylorthoformate and malononitrile and triethylorthoformate in (a) and (b) above cause allergic contact dermatitis and since they need to be isolated because of purity considerations this property creates extreme difficulties in large scale manufacture.

Method (c) noted above provides a superior end product to (a) and (b) and does so in a more economical manner, but even though the 3-amino-2-cyanoacrylamide formed en route can be reacted without isolation the intermediate (II) still requires recrystallisation, and the method also requires the preparation of formamidine.

With the methods of the present invention, not only is a superior purity end product (i.e. Allopurinol) obtained, but the process is much more economical than the prior art processes.

In its broadest aspect this invention comprises the method of preparation of novel compounds of the formula (III)

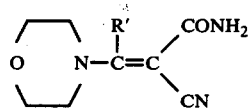

III which comprises reacting a compound R'C(OR)₃ where R is lower alkyl (methyl, ethyl, propyl, and butyl) and is preferably ethyl, and R' is hydrogen or lower alkyl (methyl, ethyl, propyl, and butyl) together with cyanoacetamide and morpholine to prepare a compound of formula III.

In the above morpholine and the compound R'C(OR)₃ are each preferably employed in a slight excess, for example about up to 20%. Also a moderately volatile polar solvent is also desirable to moderate the reaction and to improve the quality of the crystalline product. A lower alkyl alcohol such as butanol or isopropanol can be used, but acetonitrile is especially preferred for this purpose. An alcohol R OH is formed in the course of the reaction and is consequently always present in the solvent from which the product crystallizes. In the above, the morpholine acts as both a reagent and a catalyst.

A number of other amines, such as aniline, substituted anilines, piperidine, benzylamine, act in a formally similar manner to morpholine, e.g., 3-anilino-2-cyanoacrylamides are known compounds. For the present purpose, however, the stronger bases, such as piperidine and benzylamine, and the anilines suffer from serious disadvantages. For example, the anilines give "analytically" pure products at all stages but ones which are deeply colored. Removal of these colored contaminants is prohibitively expensive. The disadvantage of the stronger bases, such as piperidine, is that they also catalyze reactions of cyanoacetamide to form pyridine derivatives, which are difficult to remove and are intolerable in the final pharmaceutically active compound. Morpholine (p$K_a$, c. 8.3), however, has the advantage in that its weak basicity makes it a poor catalyst in the side reactions of cyanoacetamide. Morpholine also has the advantage that it lacks the aromatic reactivity of the anilines and thus colored by-products, which are probably polymeric, are not formed. Additionally, morpholine has the advantage that the compound of formula (III) has favorable physical properties and can be isolated readily in good yield and in high purity. Thus, the entire reaction requence to a pyrazolo[3,4-d]pyrimidine can be carried out without recrystallizations being necessary. In preparing the compound of formula III the starting materials are preferably mixed together and then heated to reflux, preferably at a temperature above about 60° C. to a temperature below about 120° C.

In order to prepare Allopurinol, the compound of formula III, in this case R' = hydrogen, is reacted with hydrazine to form the compound of formula II where R' is hydrogen and thereafter the compound of formula II is reacted with formamide and/or formic acid to form Allopurinol. The base of formula II is produced in this reaction, but is isolated as a salt, preferably a salt of a pharmaceutically acceptable acid. The present method is particularly preferred for use in the preparation of Allopurinol since a pure product is provided without necessity of isolating intermediates.

In another aspect, this invention provides a method for preparing novel and useful intermediate pyrazoles or pharmaceutically acceptable salts thereof (useful in preparing useful derivatives of Allopurinol), shown as the compounds of the formula (IV)

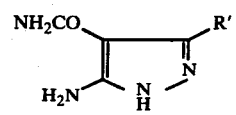

IV where R' is lower alkyl (methyl, ethyl, propyl, and butyl). These compounds are prepared by reacting hydrazine with a compound of formula III where R' is lower alkyl and defined above.

The derivatives of Allopurinol shown in formula V are then prepared by reacting a compound of the formula IV with formic acid and/or formamide as disclosed herein to prepare a compound of formula V.

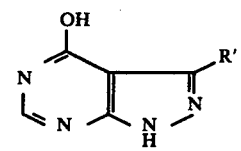

V where R' is as defined above. The drugs formed in this invention may be administered with a suitable pharmaceutically acceptable carrier in tablets, capsules or in other commonly acceptable manner.

The following examples illustrate the invention:

EXAMPLE 1

3-Morpholino-2-cyanoacrylamide

A stirred mixture of cyanoacetamide (63 g.), triethylorthoformate (134 g.), morpholine (82.5 g.) and acetonitrile (37.5 ml.) was heated under reflux for 4 hours. The initial reflux temperature was 117° C. and the final reflux temperature was 82° C.

At the end of the reflux period the mixture was cooled to 30° C. and the heavy crystalline precipitate was collected and washed with 2 × 75 ml. of ethanol. The product was dried in vacuo at 30° C. Wt. = 111 g. Yield = 82% m.p. 173°–175° C.

EXAMPLE 2

3-Aminopyrazole-4-carboxamide hemi-sulphate

To water (253 ml.) at 60° C. was added 3-morpholino-2-cyanoacrylamide (63.4 g.) and 85% technical hydrazine hydrate (22.7 g.). The mixture was rapidly heated to 95° C. and the temperature was maintained at > 90° C. for 20 minutes. The mixture was then cooled to 60° C. and the pH carefully adjusted to 1.5 by the addition of a mixture of sulphuric acid (45.7 g.) and ice (45.7 g.). The acidified reaction was cooled to 5° C. and the crystalline product collected and washed with cold water (2 × 100 ml.) and acetone (2 × 50 ml.). The product was dried in vacuo at 80° C. Wt. = 5.8 g. Yield = 95% m.p. 237°–239° C.

EXAMPLE 3

4-Hydroxypyrazolo[3,4-d]pyrimidine

A suspension of 3-aminopyrazole-4-carboxamide hemisulphate (113 g.) in formamide (325 ml.) was stirred and heated to 145° C. The reaction was held at 145° C. for 5 hours. The reaction was then cooled to 30° C. and the product collected and washed with formamide (2 × 50 ml.), water (2 × 150 ml.) and acetone (2 × 100 ml.).

Wt. of crude product = 79 gms. The crude product was recrystallized by dissolution in a solution made from sodium hydroxide (25 g.) in water (1200 ml.) with treatment at 25° C. with charcoal (8 g.), followed by reprecipitation by the addition of concentrated hydrochloric acid to pH 5. The product was collected and washed with cold water (2 × 300 ml.), acetone (2 × 200 ml.) and dried in vacuo at 60° C. Weight = 70 g. Yield = 80%.

EXAMPLE 4

3-Methyl-3-morpholino-2-cyanoacrylamide

A stirred mixture of cyanoacetamide (84 g.), triethylorthoacetate (178 g.) and morpholine (108 g.) was heated under reflux for 3 hours. The initial reflux temperature was 104° C. and the final reflux temperature was 89° C. At the end of the reflux period acetonitrile (50 ml.) was added, the mixture was cooled at 25° C., the crystalline precipitate was collected, and washed with 2 × 100 ml. of cold ethanol. Weight = 104.7 g. Yield = 53%. A sample was recrystallized from ethanol as white needles m.p. 173°–174.5° C.

EXAMPLE 5

3-Ethyl-3-morpholino-2-cyanoacrylamide

A stirred mixture of cyanoacetamide (84 g.), triethylorthopropionate (193 g.) and morpholine (108 g.) was heated under reflux for 3 hours. The initial reflux temperature was 121° C. and the final reflux temperature was 91° C. At the end of the reflux period acetonitrile (50 ml.) was added, the mixture was cooled to 25° C., the crystalline precipitate was collected, and washed with 2 × 100 ml. of cold ethanol. Weight = 87 g. Yield = 42%. A sample was recrystallized from ethanol as white needles m.p. 158° C.

EXAMPLE 6

3-morpholino-2-cyanoacrylamide (MCA)

Place 67.4 Kg. of cyanoacetamide, 143.9 Kg. of triethylorthoformate, 88.2 Kg. of morpholine and 33.0 Kg. of acetonitrile in a suitable 100 gallon reactor equipped with a stirrer and a reflux condenser.

Heat the batch to reflux and continue refluxing for 4 hours. The initial reflux temperature should be above 100° C. and the final reflux temperature should be approximately 82° C. In large scale operations such as this, it is preferable to seed the batch periodically and more preferably about every 30 minutes with 3-morpholino-2-cyanoacrylamide after initial reflux until copious precipitation is obvious.

After the reflux period is complete, preferably cool the batch rapidly to 30° C. ± 1° C. and centrifuge. The wash is a blend of a lower alcohol 74.9 Kg., 10.7 liters of water, and 10.7 Kg. of ice. Vacuum dry the MCA at 30° C.

The reflux temperature thereafter preferably should be less than about 120° C. and more than about 60° C.

EXAMPLE 7

3-aminopyrazole-4-carboxamide hemi-sulfate

Add 210.5 liters of water to the reactor and heat to 70° C. Add 52.8 Kg. of MCA and readjust the temperature to 70° C. Drain the jacket and add 18.1 Kg. of 85% hydrazine hydrate to the reactor. The heat of the reaction will cause the temperature to increase to 95°–100° C. over a 5 minute period. Ten minutes after the hydrazine addition cool the reaction to 55°–60° C. and carefully add a mixture of 37.5 Kg. of sulfuric acid and add 37.5 Kg. of ice to pH 1.5 + 0.2. Cool the batch to preferably 0°–5° C. and centrifige. Wash with 66.6 liters of water. The exact quantity of acid required may vary since there is some loss of excess hydrazine and evolved-morpholine during the course of the reaction.

EXAMPLE 8

4-hydroxypyrazolo[3,4-d]pyrimidine

Charge 244.8 Kg. of formamide and 71.6 Kg. of 3-aminopyrazole-4-carboxamide .½ $H_2SO_4$ to a well vented reactor. Heat to 140°–145° C. and hold at this temperature for five hours. Cool to preferably 5°–10° C. and centrifuge. Rinse the cake with 50.6 Kg. of formamide followed by 89.2 Kg. of water.

We claim:

1. The method of preparing a compound of the formula (I)

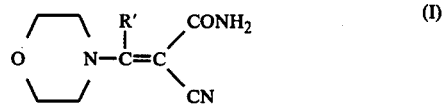

which comprises mixing together a compound of formula R'C(OR)$_3$, cyanoacetamide and morpholine, where R' is hydrogen and R is lower alkyl, and heating the mixture to a temperature above about 60° C. and below about 120° C.

2. The method of claim 1 in which R is ethyl.

3. The method of claim 1 in which a polar solvent is used.

4. The method of claim 1 in which the batch is seeded periodically with the compound of formula I.

5. The method of claim 3 in which acetonitrile is used as the solvent.

6. The method of claim 4 in which a polar solvent is used.

7. The method of claim 5 in which acetonitrile is used as the solvent.

* * * * *